(12) United States Patent
Broom et al.

(10) Patent No.: US 9,855,034 B2
(45) Date of Patent: Jan. 2, 2018

(54) TISSUE FIXATION DEVICE

(71) Applicant: Covidien LP, Mansfield, MA (US)

(72) Inventors: Daniel Broom, Branford, CT (US); Joshua Stopek, Minneapolis, MN (US); Timothy Sargeant, Guilford, CT (US); Nicholas Maiorino, Branford, CT (US); Arpan Desai, Hamden, CT (US); Saumya Banerjee, Hamden, CT (US); Timothy Flavin, Evanston, IL (US)

(73) Assignee: Covidien LP, Mansfield, MA (US)

( * ) Notice: Subject to any disclaimer, the term of this patent is extended or adjusted under 35 U.S.C. 154(b) by 215 days.

(21) Appl. No.: 14/389,840

(22) PCT Filed: Aug. 20, 2013

(86) PCT No.: PCT/US2013/055723
§ 371 (c)(1),
(2) Date: Oct. 1, 2014

(87) PCT Pub. No.: WO2014/031599
PCT Pub. Date: Feb. 27, 2014

(65) Prior Publication Data
US 2015/0073473 A1    Mar. 12, 2015

Related U.S. Application Data

(60) Provisional application No. 61/692,351, filed on Aug. 23, 2012.

(51) Int. Cl.
*A61B 17/04* (2006.01)
*A61B 17/06* (2006.01)
(Continued)

(52) U.S. Cl.
CPC .... *A61B 17/06166* (2013.01); *A61B 17/0401* (2013.01); *A61B 17/0469* (2013.01);
(Continued)

(58) Field of Classification Search
CPC ............ A61B 17/0401; A61B 17/0469; A61B 17/06166; A61B 2017/0406;
(Continued)

(56) References Cited

U.S. PATENT DOCUMENTS 3,985,138 A    10/1976  Jarvik
2004/0088008 A1  5/2004  Gannoe et al.
(Continued)

FOREIGN PATENT DOCUMENTS

KR    101132841 B1   4/2012
WO    99/59477 A1    11/1999
WO    WO01/28457 A1  4/2001

OTHER PUBLICATIONS

European Search Report EP13831240.0 dated Apr. 21, 2016.
(Continued)

*Primary Examiner* — Robert Lynch

(57) ABSTRACT

A tissue fixation device includes an elongated body defining a longitudinal axis and including a proximal end and a distal end. At least two barbed segments diverge distally away from the distal end of the elongated body and a pledget is disposed at distal ends of the barbed segments. The elongated body, barbed segments, and pledget are provided in a variety of configurations depending upon the performance requirements desired of the tissue fixation device for the envisaged application of use.

20 Claims, 3 Drawing Sheets

(51) Int. Cl.
*A61B 17/00* (2006.01)
*A61F 2/00* (2006.01)

(52) U.S. Cl.
CPC ..... *A61B 17/0057* (2013.01); *A61B 17/00234* (2013.01); *A61B 2017/00597* (2013.01); *A61B 2017/00628* (2013.01); *A61B 2017/00663* (2013.01); *A61B 2017/00876* (2013.01); *A61B 2017/0406* (2013.01); *A61B 2017/0412* (2013.01); *A61B 2017/0464* (2013.01); *A61B 2017/06176* (2013.01); *A61F 2/0063* (2013.01); *A61F 2220/0016* (2013.01)

(58) Field of Classification Search
CPC ... A61B 2017/0412; A61B 2017/06176; A61F 2/0063
See application file for complete search history.

(56) References Cited

U.S. PATENT DOCUMENTS

| | | | | |
|---|---|---|---|---|
| 2005/0182446 | A1* | 8/2005 | DeSantis | A61B 17/06066 606/222 |
| 2005/0283246 | A1 | 12/2005 | Cauthen et al. | |
| 2006/0235447 | A1 | 10/2006 | Walshe | |
| 2009/0044814 | A1* | 2/2009 | Iancea | A61B 17/06109 128/848 |
| 2009/0248067 | A1* | 10/2009 | Maiorino | A61B 17/0401 606/228 |
| 2009/0299407 | A1* | 12/2009 | Yuan | A61B 17/06166 606/228 |
| 2009/0306681 | A1* | 12/2009 | Del Nido | A61B 17/0401 606/139 |
| 2010/0274283 | A1 | 10/2010 | Kirsch et al. | |
| 2011/0054522 | A1 | 3/2011 | Lindh, Sr. et al. | |
| 2011/0087249 | A1* | 4/2011 | Rodrigues | A61B 17/0401 606/151 |
| 2015/0366553 | A1* | 12/2015 | Kim | A61B 17/06109 606/230 |

OTHER PUBLICATIONS

International Search Report for PCT/US13/55723 date of completion is Nov. 1, 2013 (4 pages).
Australian Examination Report dated Feb. 21, 2017 issued in corresponding Australian Application No. 2013305934.
European Examination Report dated Sep. 21, 2017 issued in corresponding European Application No. 13 831 240.0.

* cited by examiner

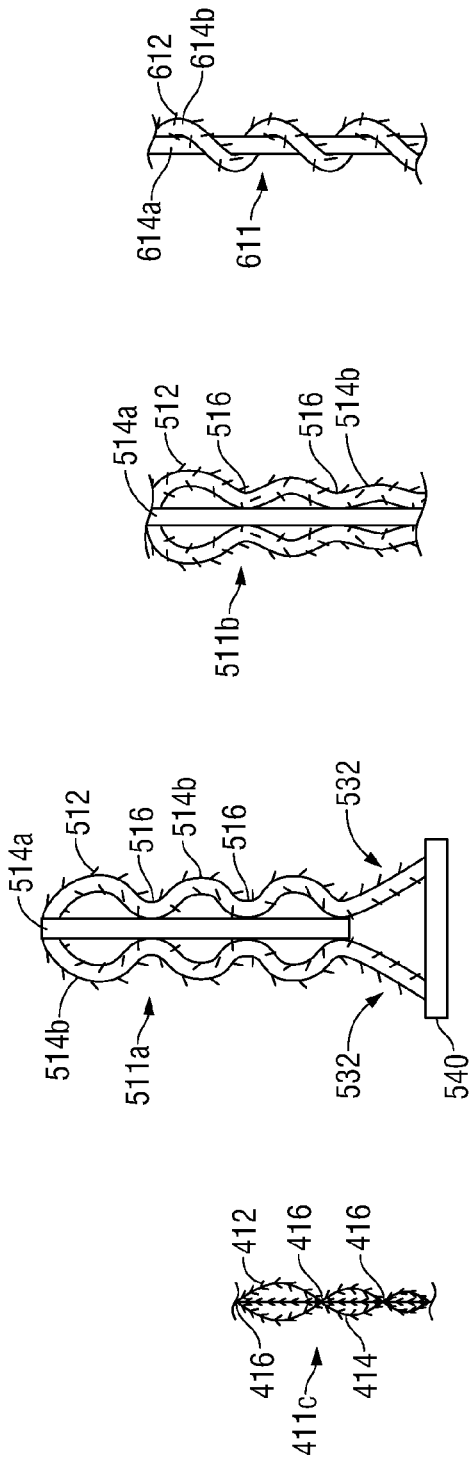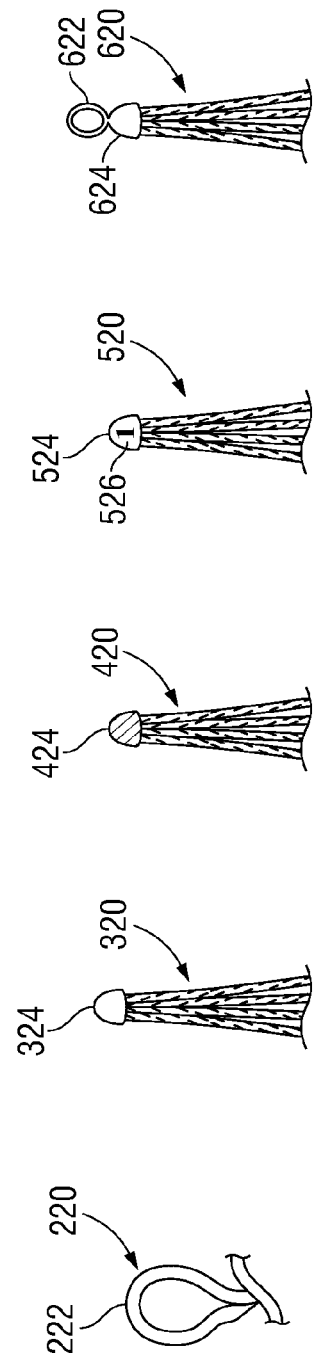

TISSUE FIXATION DEVICE

CROSS-REFERENCE TO RELATED APPLICATIONS

This application is a National Stage Application of PCT/US13/55723 under 35USC §371 (a), which claims the benefit of and priority to U.S. Provisional Patent Application No. 61/692,351, filed Aug. 23, 2012, the entire disclosure of which is incorporated by reference herein.

BACKGROUND

Technical Field

The present disclosure relates to medical devices and methods of using the same. More particularly, the present disclosure relates to surgical devices for tissue fixation.

Background of Related Art

Techniques for repairing damaged or diseased tissue are widespread in medicine. Wound closure devices, such as sutures and staples, as well as other repair devices like mesh or patch reinforcements, are frequently used for repair. For example, in the case of hernias, a surgical mesh or patch is commonly used to reinforce the abdominal wall. Typically, sutures, staples, and/or tacks are utilized to fix the surgical mesh or patch to surrounding tissue.

The current standard of care for laparoscopic ventral hernia repair, for example, involves the application of stay sutures that are placed both through a surgical mesh and trans-abdominally, and tied down just underneath the skin. Permanent sutures are typically used for this application. The sutures are placed around the perimeter of the mesh, and sometimes in the center to permanently tie the mesh to the area of herniation and to prevent the mesh from sliding within the peritoneum. For each stay suture, a surgeon will pierce the abdominal wall with a suture passer and grasp one end of a suture that has been pre-placed on the mesh, and pull the end of the suture through the abdominal wall and out past the skin. When the two ends of the suture are outside of the patient, the surgeon will pull up on the mesh and tie down a knot in the suture, compressing the abdominal wall and keeping the mesh tight against the peritoneum. The surgeon will then cut the excess suture and close the skin over the knot. This process may take about a minute or two for each stay suture, and may be associated with acute and/or chronic pain, likely due to compression of the abdominal wall and the nerves within it.

It would be advantageous to provide a fixation device that simplifies and shortens the time to secure a mesh, and limits or prevents pain caused by abdominal wall and nerve compression.

SUMMARY

A tissue fixation device includes an elongated body extending between a proximal end and a distal end, at least two barbed segments diverging distally away from the distal end of the elongated body, and a pledget disposed at distal ends of the barbed segments. The elongated body, barbed segments, and pledget are provided in a variety of configurations.

The barbed segments may be chemically, thermally, or mechanically attached to the pledget. In embodiments, the distal ends of the barbed segments are melt pressed onto the pledget. In some embodiments, the pledget may include a plurality of openings, through which the distal ends of the barbed segments may extend.

The pledget may include a biocompatible coating. In embodiments, the coating is anti-adhesive, and in some embodiments, the coating may include surface reactive functional groups. In embodiments, the pledget may be magnetic. The pledget may also include barbs and/or darts to mechanically fix the pledget to tissue.

The elongated body may be formed from a single filament or multiple filaments that may each be barbed or unbarbed, and arranged to intersect or remain separate along a length thereof. The filament(s) may be formed from biodegradable and/or non-biodegradable polymeric and/or metallic materials. In embodiments, filaments of the elongated body may extend distally beyond the elongated body to define the barbed segments.

The proximal portion of the elongated body may terminate in a blunt tip, or may be provided in other configurations, such as a loop. The proximal portion may be free of barbs and a needle. In embodiments, the proximal portion may include a cap. The cap may be magnetic or include a ring extending from a proximal end thereof to aid a clinician in placing the tissue fixation device within tissue. The proximal portion may also include indicia.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 6A-6H are side views of various embodiments of body sections of a tissue fixation device of the present disclosure; and FIGS. 7A-7E are side view of various embodiments of a proximal portion of a tissue fixation device of the present disclosure.

DETAILED DESCRIPTION

Figure 1:
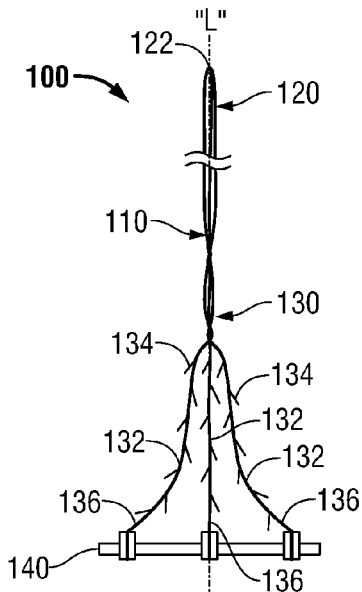
FIG. 1 is a side view of a tissue fixation device in accordance with an embodiment of the present disclosure.

A tissue fixation device and method of using the same are described herein. While the present discussion and figures below depict exemplary embodiments of the present disclosure in terms of a tissue fixation device for use in hernia repair, the presently disclosed devices may be utilized in any surgical procedure requiring joining or positioning of tissue, or fastening of surgical implants thereto.

A tissue fixation device in accordance with the present disclosure includes an elongated body extending between a proximal end and a distal end, and at least two barbed segments diverging distally away from the distal end of the elongated body and including distal ends secured to a pledget. The tissue fixation device described herein may be formed from any sterilizable biocompatible material that has suitable physical properties for the intended use of the device. The elongated body, barbed segments, and/or pledget of the tissue fixation device may be fabricated from any biodegradable and/or non-biodegradable polymeric and/or metallic material that can be used in surgical procedures.

The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers include polyhydroxy acids prepared from lactone monomers such as glycolide, lactide, caprolactone, ε-caprolactone, valerolactone, and δ-valerolactone, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly (glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; poly-ortho esters; and copolymers, block copolymers, homopolymers, blends, and combinations thereof.

Some non-limiting examples of suitable non-degradable materials include: polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

In embodiments, the elongated body, barbed segments, pledget, or portions thereof may be formed from polybutester, a copolymer of butylenes terephthalate and polytetramethylene ether glycol. For example, the tissue fixation device, or portions thereof, may be formed from the commercially available nonabsorbable polybutester monofilaments, sold under the trade name Novafil™ by Covidien. In some embodiment, the tissue fixation device, or portions thereof, may be formed from a copolymer of glycolic acid and trimethylene carbonate, such as, for example, Maxon™, commercially available from Covidien. In embodiments, the tissue fixation device, or portions thereof, may be formed from a terpolymer of glycolic acid, trimethylene carbonate, and dioxanone, such as, for example, Biosyn™, commercially available from Covidien.

In embodiments, the tissue fixation device may include: metals such as steel or titanium; metal alloys including degradable alloys such as iron-based or magnesium-based degradable alloys; and the like.

The elongated body and/or barbed segments of the tissue fixation device described herein may be formed from monofilament or multi-filament structures that are fabricated from natural, synthetic, degradable, and/or non-degradable materials, as well as combinations thereof, as described above. The elongated body and/or barbed segments may be formed using any technique within the purview of those skilled in the art such as, for example, extrusion, molding, casting, and/or spinning. Where the elongated body and/or barbed segments are made of multiple filaments, the elongate body and/or barbed segments may be formed using any known technique such as, for example, braiding, weaving or knitting. The filaments may also be drawn, oriented, annealed, calendared, crinkled, twisted, commingled, or air entangled to form the elongated body and/or barbed segments.

In embodiments, the elongated body, or portions thereof, may be barbed. The barbs may be single or compound barbs formed along a portion or the entire length of the elongated body in specified or random patterns. Barbs may be formed from angled cuts in an outer surface of the elongated body, or barbs may be molded on the outer surface of the elongated body, such that an inner surface of the barb is positioned opposite to an outer surface of the elongated body. The barbs may all be oriented in the same or different directions, and may be cut at the same or different barb angles. Compound barbs include an inner surface including at least two angled cuts disposed at first and second orientations, respectively, relative to a longitudinal axis of the elongated body. Examples of compound barbs which may be utilized include those disclosed in U.S. Patent Application Publication No. 2009/0210006, entitled "Compound Barb Medical Device and Method", the entire disclosure of which is incorporated by reference herein.

The surface area of the barbs may vary. For example, fuller-tipped barbs can be made of varying sizes designed for specific surgical applications. When joining fat and relatively soft tissues, large barbs may be desired, whereas smaller barbs may be more suitable for collagen-dense tissues. In some embodiments, a combination of large and small barbs on the same structure may be beneficial, for example, when used in a tissue repair with differing tissue layer structures. A combination of large and small barbs may be used within the same tissue fixation device such that the barb sizes are customized for each tissue layer to ensure maximum holding properties.

Referring now to the drawings, FIG. 1 illustrates a tissue fixation device 100 of the present disclosure. Tissue fixation device 100 includes an elongated body 110 defining a longitudinal axis "L" and having a proximal end 120 and a distal end 130. The elongated body 110 extends between the proximal end 120 and the distal end 130, and is illustrated as a solid structure that is free of barbs. Although shown as having a substantially circular cross-sectional geometry, the elongated body portion may be any suitable shape, such as round, elliptical, square, flat, octagonal, and rectangular, among other geometric and non-geometric shapes. In embodiments, the elongated body 110 may have a varying diameter, e.g., the elongated body may have a smaller diameter at a proximal end that gradually transitions to a larger diameter at a distal end.

Proximal end 120 of the elongated body 110 may terminate in a blunt tip 122. The proximal end may be a component separate from, and joined to, the elongated body, or monolithically formed with the elongated body. Distal end 130 includes at least two barbed segments 132 extending distally from the elongated body 110, and terminating at a pledget 140. Barbs 134 may be disposed on any portion of a barbed segment 132, in embodiments, barbs 134 are disposed only on a portion of the barbed segments 132 closest to the elongated body 110, for example, up to about half of the length of the barbed segment 132 extending from the elongated body 110. As illustrated, barbs 134 extend along the entire length of the barbed segments 132.

The barbed segments 132 extend from the distal end 130 of the elongated body 110. The barbed segments may be permanently or releasably secured to the elongated body by convention means, such as, for example, ultrasonic welding or with the use of adhesives, or may be integrally formed with the elongated body. The barbed segments may be formed from the same or different materials than that of the elongated body.

A pledget may be formed from plastic, polymeric, or other biocompatible materials, including non-degradable and/or degradable materials as described above. For example, in embodiments in which the distal portion of the tissue fixation device is fabricated from a non-degradable material, a non-degradable pledget may be utilized, such as a pledget fabricated from a silicone or fluorocarbon based material, like polytetrafluoroethylene (e.g., TEFLON). Similarly, in some embodiments in which the distal portion of the tissue fixation device is fabricated from a biodegradable material, a biodegradable pledget may be utilized, such as a pledget fabricated from a copolymer of lactide and glycolide.

In embodiments, a pledget may include magnetic material to aid a clinician in positioning the pledget against tissue with the use of an external magnet. A pledget may be fabricated from an absorbable and/or non-absorbable magnet material, such as a ferromagnetic metal. Suitable metals include iron ore (magnetite or lodestone), cobalt and nickel, rare earth metals like gadolinium and dysprosium, and alloys thereof. The pledget may also be made from composite materials such as ceramic or ferrite, alnico (a combination of aluminum, nickel and cobalt with iron), or triconal (a combination of titanium, cobalt, nickel and aluminum with iron). In some embodiments, a pledget may be formed from a polymeric material including ferromagnetic metal particles. The polymer may be any biodegradable and/or non-biodegradable polymer as described above. In embodiments, ferromagnetic metal particles may be freely admixed or co-extruded with the polymer forming the pledget, or may be tethered to the polymer through any suitable chemical bond. In some embodiments, the ferromagnetic metal particles may be spray or dip coated on a formed pledget.

Figure 2:
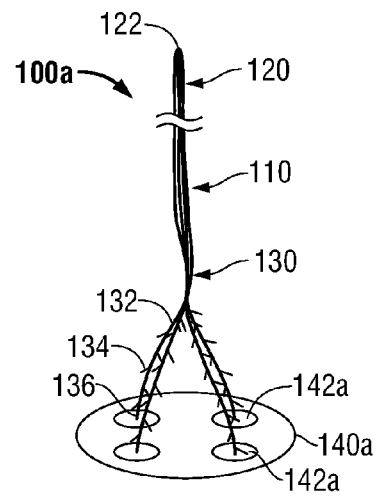
FIG. 2 is a perspective view of a tissue fixation device in accordance with another embodiment of the present disclosure.

Distal ends 136 of the barbed segments 132 may be secured to the pledget 140 in a variety of ways. As illustrated in FIG. 1, the distal ends 136 of the barbed segments 132 may be secured to pledget 140 by chemically or thermally binding the barbed segments 132 to the pledget 140, such as by use of an adhesive, such as a hot melt adhesive, or by applying a binder, such as a powder, paste, or melt, and melting the binder to secure the barbed segments 132 to the pledget 140. In embodiments, the barbed segments and pledget may also be secured mechanically. As illustrated in FIG. 2, tissue fixation device 100a, which is substantially similar to tissue fixation device 100 of FIG. 1, includes a pledget 140a including openings 142a that are dimensioned to receive the distal end 136 of the barbed segment 132. The distal ends 136 of the barbed segments 132 may be secured within the opening 142a, such as by molding the pledget 140a around the distal end 136 so that the pledget 140a frictionally engages the barbed segments 132, or by knotting the distal ends 136 of the barbed segments 132 through the openings 142a, for example. While the openings 142a are illustrated as being radially disposed around the pledget 140a so that the barbed segments 132 form a taper from the pledget 140 towards the elongated body 110, it should be understood that the arrangement of the openings 142a in the pledget may vary, depending upon the desired structure of the tissue fixation device.

In embodiments, a pledget may include a coating. The coating may be utilized to alter the physical properties on the surface of the pledget (e.g., enhance lubricity), or may provide a therapeutic benefit to tissue. In general, a coating may be applied to a surface of the pledget, or selective regions thereof, by, for example, spraying, dipping, brushing, vapor deposition, co-extrusion, capillary wicking, film casting, molding, etc.

Therapeutic agents include any substance or mixture of substances that have clinical use. Alternatively, a therapeutic agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of therapeutic agents may be coated on a pledget, or incorporated into the tissue fixation device of the present disclosure. Moreover, any agent which may enhance tissue repair, limit the risk of sepsis, and modulate the mechanical properties of the tissue fixation device (e.g., the swelling rate in water, tensile strength, etc.) may be added to the material forming the tissue fixation device or may be coated thereon.

Examples of classes of therapeutic agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of therapeutic agents may be used.

Other therapeutic agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable therapeutic agents which may be included in the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

Figure 3A:
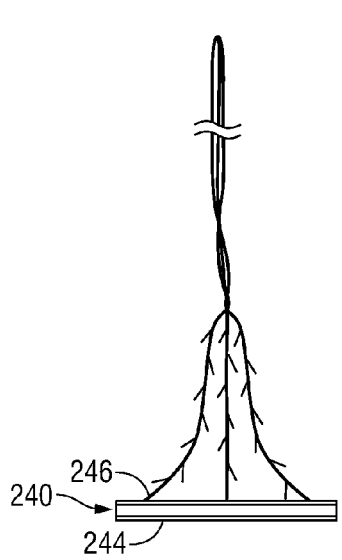
FIGS. 3A-3C are views of various embodiments of a distal portion of a tissue fixation device of the present disclosure.

As illustrated in FIG. 3A, a bottom surface 244 of a pledget 240 may include an anti-adhesive coating that acts as a barrier layer between the tissue fixation device and surrounding tissue to prevent the formation of adhesions, and a top surface 246 of the pledget 440 may be surface treated in order to promote adhesion to tissue. In embodiments, the top surface 246 may include a coating containing tissue reactive functional groups for fixation of the pledget 240 to tissue by crosslinking with reactive groups present in tissue such as primary amine groups, secondary amine groups, hydroxyl groups, carboxylic groups, sulfonic groups, combinations thereof, and the like. Such groups include compounds possessing chemistries having some affinity for tissue.

Figure 3B:
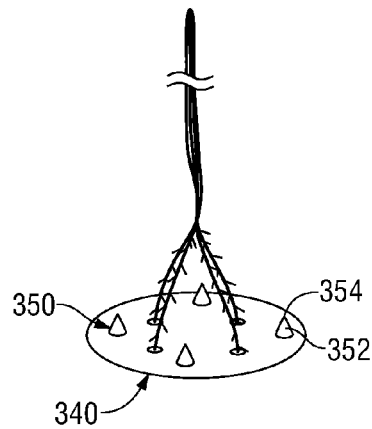
Figure 3C:
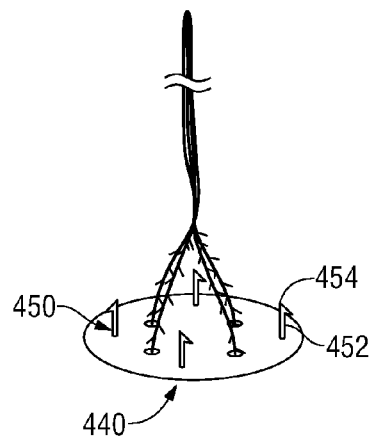

FIGS. 3B and 3C illustrate a distal portion including a pledget having mechanical means of attachment to tissue. The pledget may include mechanical barbs, grips, hooks, or darts to achieve, or enhance, adhesivity to tissue. As illustrated in FIG. 3B, a pledget 340 may include a plurality of mechanical darts 350, each including a base portion 352 tapering toward a sharp tip 354. The base portion 352 includes a larger diameter than the tip 354 for enhanced tissue fixation. As illustrated in FIG. 3C, pledget 440 may include mechanical darts 450, each dart 450 including an arm 452 having a sharp or pointed tip 454 for piercing and gripping tissue.

Figure 4A:
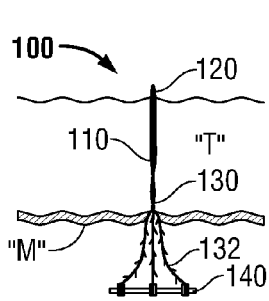
FIGS. 4A-4C are schematic illustrations of an exemplary method of using a tissue fixation device of the present disclosure.
Figure 4B:
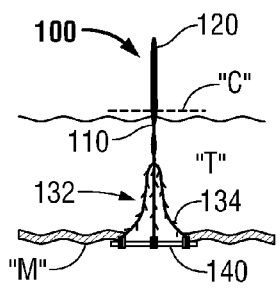
Figure 4C:
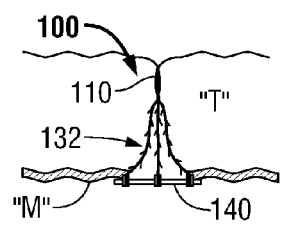

FIGS. 4A-4C illustrate an exemplary method for fixing a hernia mesh "M" to tissue "T" with a tissue fixation device of the present disclosure. As illustrated in FIG. 4A, tissue fixation device 100 is delivered to a surgical site and positioned with the elongated body 110 and proximal portion 120 extending through the tissue "T", the distal end 130 abutting hernia mesh "M", and the barbed segments 132 and pledget 140 being positioned below the fascia. The tissue fixation device 100 may be delivered to the surgical site using a conventional suturing device, such as an Endo Close™ Single Use Suturing Device, commercially available from Covidien. For example, the tissue fixation device 100a may be hooked through a portion of a stylet of the Endo Close™ device and drawn within the cannula of the device. The Endo Close™ device may then be inserted through the tissue and released under the fascia without the need for a sharp piercing tip on the proximal portion of the tissue fixation device.

After the tissue fixation device 100 is delivered through the tissue "T", a clinician may pull up on the proximal portion 120 of the tissue fixation device 100 such that the pledget 140 is compressed against the hernia mesh "M" and tissue "T", as illustrated in FIG. 4B. The barbs 134 located on the barbed segments 132 of the tissue fixation device 100 adhere to the hernia mesh "M" and/or tissue "T", fixing the pledget 140 thereagainst. The clinician may then cut the proximal portion 120, or a portion of the elongated body 110, for example, along cut line "C", allowing the tissue fixation device 100 to hold the hernia mesh "M" against tissue "T", as illustrated in FIG. 4C, without compressing the tissue "T" with a suture knot, as required by traditional devices. In embodiments, the proximal portion 120 may be formed from a biodegradable material and the barbed segments 132 may be formed from a non-degradable material to aid in patient comfort by limiting the mass of the tissue fixation device within the tissue while retaining fixation integrity of the hernia mesh "M".

Figure 5A:
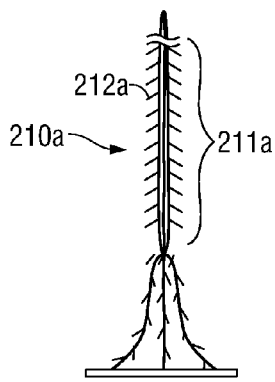
FIGS. 5A-5C are side view of embodiments of the elongated body of a tissue fixation device of the present disclosure.
Figure 5B:
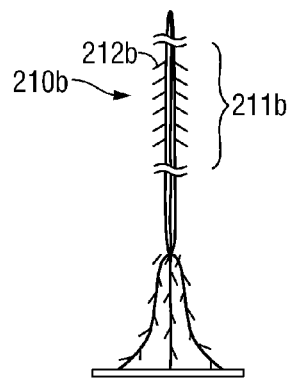
Figure 5C:
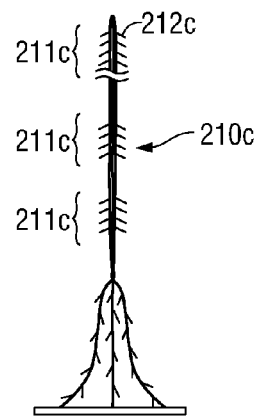

The elongated body of the tissue fixation device of the present disclosure may be provided in a variety of configurations. The elongated body may include body sections having a structure, such as barbs and/or multi-filaments segments, that is different from that of the monofilament structure of FIG. 1. The body sections may extend along the entire length of the elongated body, or along portion(s) thereof. For example, as illustrated in FIG. 5A, an elongated body 210a may include a body section 211a including barbs 212a extending along the entire length thereof to aid in fixing the tissue fixation device within tissue. In some embodiments, as illustrated in FIG. 5B, a body section 211b including barbs 212b may be provided on only a select portion of the elongated body 210b. And in other embodiments, as illustrated in FIG. 5C, body sections 211c including barbs 212c may be provided in spaced intervals along the length of the elongated body 210c. As described above with respect to the barbs of the distal portion of the tissue fixation device, the barbs of the elongated body may also be provided with any barb configuration (e.g., single or compound), in any pattern thereon.

Figure 6A:
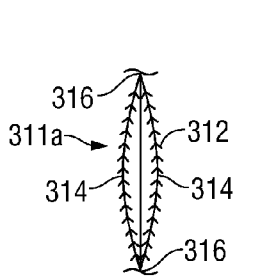
Figure 6B:
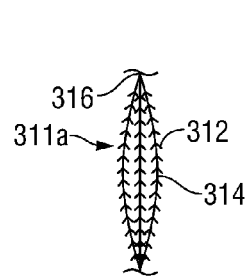

FIGS. 6A-H illustrate exemplary embodiments of other body sections that may be incorporated into an elongated body of the present disclosure. As illustrated in FIG. 6A, for example, a body section 311a may include a combination of barbed and unbarbed filaments 314 that are substantially separate and in spaced relation to each other along a majority of the length thereof, and united only at pre-defined points 316 positioned at opposed terminal ends of the body section 311a. The filaments 314 may be bonded, welded, fused, knotted, braided, twisted, entangled, or otherwise joined at the pre-defined points 316. FIG. 6B differs from FIG. 6A in that all of the filaments 314 of the body section 311b in FIG. 6B include barbs 312.

Figure 6C:
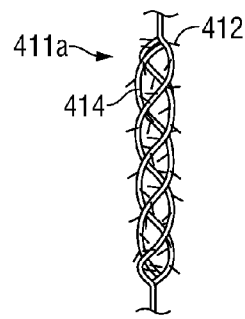
Figure 6D:
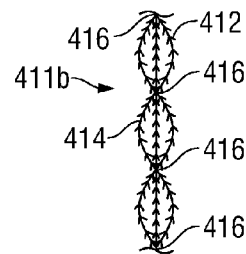

Alternatively, as illustrated in FIGS. 6C-6H, filaments may be commingled along the length of a body section. FIG. 6C illustrates a body section 411a including a plurality of filaments 414 each including barbs 412 in a braided configuration. FIG. 6D illustrates a body section 411b including a plurality of filaments 414 that intersect at least one other filament at pre-defined points 416 along the length of the body section 411b. As shown, all filaments 414 intersect at pre-defined points 416 that are substantially evenly spaced along the length of the body section 411b. In other embodiments, the pre-defined points may be unevenly spaced along the length of the body section. As shown in FIG. 6E, for example, varying the spacing between pre-defined points 416 may provide the body section 411c with a tapered or varied shape along the length thereof.

FIG. 6F illustrates a body section 511a including a plurality of filaments 514 including a central filament 514a and at least one outer filament 514b. The outer filament 514b is joined to the central filament 514a at pre-defined points 516 therealong, such as by fusing the central filament 514a and the outer filament 514b together. The central filament 514a is illustrated as being free of barbs and the outer filaments 514b as including barbs 512. In embodiments, the central filament 514a may be formed from a non-absorbable material and the outer filaments 514b may be formed from an absorbable material. In some embodiments, the central filament 514a may have a larger diameter than the outer filaments 514b. As illustrated, outer filaments 514b extend distally beyond the central filament 514a to form the barbed segments 532 which are attached to pledget 540. In other embodiments, as illustrated in FIG. 6G, the shape of the body section 511b may be varied by varying the length of the outer filaments 514b provided between the pre-defined points 516.

FIG. 6H illustrates a body section 611 including a central filament 614a and an outer filament 614b twisted around the central filament 614a. As illustrated, the central filament 614 is free of barbs and the outer filament 614b includes barbs 612, however, it is envisioned that any barbed/unbarbed configuration of filaments may be utilized. It should be understood that the body section may include any number of barbed and/or unbarbed filaments that are gathered in a variety of configurations. The filaments may all be fabricated from the same or different materials, and be of the same or different cross-sectional diameter or size. It should also be understood that the barbed segments may include any of the configurations of the body section of the elongated body illustrated above.

Referring again to FIG. 1, the proximal end 120 is illustrated terminating in an unsharpened tip 122. The proximal end of the tissue fixation device may also be provided in a variety of other configurations having a blunted tip, such as that shown in FIG. 7A. As illustrated in FIG. 7A, a proximal portion 220 may be formed into a loop 222. As illustrated in FIG. 7B, a proximal portion 320 may terminate in a cap 324. The cap may be formed from any polymeric and/or metallic material as described above, and in embodiments in which the elongated body is formed from a plurality of filaments, may be utilized to gather and crimp the filament together at a terminal end thereof.

In embodiments, as illustrated in FIG. 7C, the cap 424 of a proximal portion 420 may be formed from a magnetic material, such as those described above in reference to the pledget of the distal portion.

In embodiments, the cap may include indicia, such as shapes, symbols, numerals, text, among other markings, for identifying the proximal portion of the tissue fixation device. FIG. 7D illustrates a proximal portion 520 including a cap 524 including indicia 526. The indicia may be in any shape and size to provide a visibly distinguishable mark or pattern on the proximal portion of the tissue fixation device. In embodiments, indicia may be applied by utilizing ink that may be visualized under visible, infrared, ultraviolet, and/or by other wavelengths of light. In some embodiments, dyes may be utilized. Dyes include, but are not limited to, carbon black, bone black, FD&C Blue #1, FD&C Blue #2, FD&C Blue #3, FD&C Blue #6, D&C Green #6, D&C Violet #2, methylene blue, indocyanine green, other colored dyes, and combinations thereof. It is envisioned that visualization agents may also be used, such as fluorescent compounds (e.g., fluorescein or eosin), x-ray contrast agents (e.g., iodinated compounds), ultrasonic contrast agents, and MRI contrast agents (e.g., Gadolinium containing compounds). A variety of applicators within the purview of those skilled in the art may be used to apply the indicia, including, for example, syringes, droppers, markers or pen-like applicators, brushes, sponges, patches, combinations thereof, and the like.

FIG. 7E illustrates a proximal portion 620 including a cap 624 having a ring 622 extending proximally therefrom. A ring 622 may be utilized to aid a clinician in pulling a tissue fixation device up through tissue, as described above with respect to the exemplary method of using a tissue fixation device as described above.

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A tissue fixation device comprising:
an elongated body formed from at least one filament, the elongated body defining a longitudinal axis and including a proximal end and a distal end;

first, second, and third barbed segments diverging distally away from the distal end of the elongated body, the first, second, and third barbed segments terminating at respective first, second, and third distal ends; and a pledget including a proximal surface and a distal surface, the first, second, and third distal ends of the first, second, and third barbed segments secured to the proximal surface of the pledget in spaced relation relative to an outer perimeter defined around the proximal and distal surfaces of the pledget and to each other such that the first, second, and third barbed segments form a taper in the tissue fixation device from the pledget towards the elongated body.

2. The tissue fixation device of claim 1, wherein the proximal end of the elongated body includes a loop.

3. The tissue fixation device of claim 2, wherein the loop is free of barbs.

4. The tissue fixation device of claim 1, further including a cap disposed over the proximal end of the elongated body, the cap having a generally hemispherical profile terminating in a blunt tip.

5. The tissue fixation device of claim 4, wherein the cap is magnetic.

6. The tissue fixation device of claim 4, wherein a ring extends from a proximal end of the cap.

7. The tissue fixation device of claim 1, wherein the proximal surface of the pledget includes at least one dart extending proximally therefrom.

8. The tissue fixation device of claim 7, wherein the dart terminates in a sharp tip.

9. The tissue fixation device of claim 1, wherein the pledget includes surface reactive functional groups.

10. The tissue fixation device of claim 1, wherein the pledget is magnetic.

11. The tissue fixation device of claim 1, wherein the elongated body is a monofilament structure.

12. The tissue fixation device of claim 1, wherein the elongated body includes barbs.

13. The tissue fixation device of claim 1, wherein the elongated body includes a plurality of filaments.

14. The tissue fixation device of claim 13, wherein at least one of the plurality of filaments includes barbs.

15. The tissue fixation device of claim 14, wherein the barbs are compound barbs.

16. The tissue fixation device of claim 14, wherein the filaments of the elongated body are tethered at the proximal and distal ends.

17. The tissue fixation device of claim 16, wherein the plurality of filaments are one of twisted, braided, intertwined, and entangled.

18. The tissue fixation device of claim 1, wherein the elongated body includes a central filament defining a central axis and at least one barbed filament secured to the central filament at pre-determined points along the central axis.

19. The tissue fixation device of claim 18, wherein the elongated body includes two barbed filaments, the barb filaments extending distally beyond the central filament to define the barbed segments.

20. The tissue fixation device of claim 1, wherein the first and second distal ends of the first and second barbed segments are chemically or thermally bound to the pledget.

* * * * *